United States Patent [19]

Kelly

[11] 4,081,594

[45] Mar. 28, 1978

[54] UNSATURATED BICYCLIC LACTONE INTERMEDIATES FOR PREPARING PGC-TYPE COMPOUNDS

[75] Inventor: Robert C. Kelly, Kalamazoo, Mich.

[73] Assignee: The Upjohn Company, Kalamazoo, Mich.

[21] Appl. No.: 710,622

[22] Filed: Aug. 2, 1976

Related U.S. Application Data

[62] Division of Ser. No. 415,050, Nov. 12, 1973, Pat. No. 3,993,686.

[51] Int. Cl.$^2$ ............................................. C07D 307/77
[52] U.S. Cl. ............................. 542/429; 260/343.3 P
[58] Field of Search ..................... 260/343.3 P, 240 R; 542/429

[56] References Cited

U.S. PATENT DOCUMENTS

| 3,864,387 | 2/1975 | Nelson | 260/343.3 P |
| 3,872,149 | 3/1975 | Crabbe | 260/343.3 P |

OTHER PUBLICATIONS

Crabbe et al., Tetrahedron letters No. 32, pp. 3021-3022 (1973).

*Primary Examiner*—Natalie Trousof
*Assistant Examiner*—Jane T. Fan
*Attorney, Agent, or Firm*—Robert A. Armitage; Ward F. Nixon

[57] ABSTRACT

Process for the total synthesis of 11,12-unsaturated prostaglandin compounds, i.e., prostaglandin $C_2$ type compounds and analogs, and to certain novel compounds and intermediates produced thereby. The compounds produced by said process are useful as vasodepressors and antisecretory agents, and in managing cases of renal disfunction.

17 Claims, No Drawings

UNSATURATED BICYCLIC LACTONE INTERMEDIATES FOR PREPARING PGC-TYPE COMPOUNDS

The present application is a divisional application of Ser. No. 415,050, filed Nov. 12, 1973, issued as U.S. Pat. No. 3,993,686, on Nov. 23, 1976.

The present invention relates to intermediates for the preparation of prostaglandin $C_2$ compound, for which the essential material constituting disclosure therefor is incorporated by reference here from U.S. Pat. No. 3,993,686.

I claim:

1. An optically active compound of the formula:

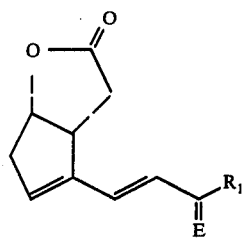

or a racemic compound of that formula and the mirror image thereof, wherein E is

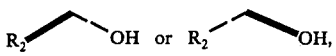

in which $R_2$ is hydrogen or lower alkyl of 1 to 4 carbon atoms, inclusive, and $R_1$ is

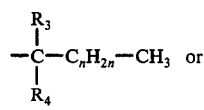

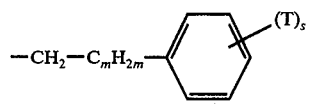

in which $R_3$ and $R_4$ are each hydrogen, fluoro or lower-alkyl of 1 to 4 carbon atoms, inclusive, with the proviso that $R_3$ is fluoro only when $R_4$ is hydrogen or fluoro; $—C_nH_{2n}—$ is straight chain alkylene of 1 to 5 carbon atoms, inclusive; $—C_mH_{2m}—$ is a valance bond or alkylene of 1 to 9 carbon atoms, inclusive, with 1 to 6 carbon atoms, inclusive, between $—CH_2—$ and the ring; and T is lower-alkyl of 1 to 4 carbon atoms, inclusive, fluoro, chloro, trifluoro-, methyl, or $—OR_2$, in which $R_2$ is hydrogen or lower-alkyl of 1 to 4 carbon atoms, inclusive, and $s$ is 0 to 3, inclusive, with the proviso that not more than two T's are other than alkyl.

2. An optically active compound according to claim 1, wherein E is

3. A compound according to claim 2, wherein $R_1$ is

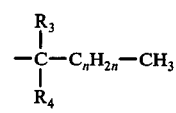

in which $—C_nH_{2n}—$ is trimethylene.

4. A compound according to claim 3, wherein $R_3$ and $R_4$ are each hydrogen.

5. A compound according to claim 3, wherein $R_3$ is hydrogen and $R_4$ is fluoro.

6. A compound according to claim 3, wherein $R_3$ is hydrogen and $R_4$ is methyl.

7. A compound according to claim 3 wherein $R_3$ and $R_4$ are each methyl.

8. A compound according to claim 2, wherein $R_1$ is

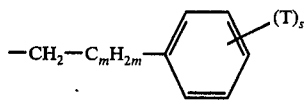

in which $—C_mH_{2m}—$ is methylene.

9. A compound according to claim 8 wherein $s$ is 0.

10. An optically active compound according to claim 1, wherein E is

in which $R_2$ is methyl or ethyl.

11. A compound according to claim 10, wherein $R_1$ is

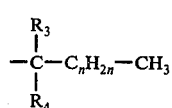

in which $—C_nH_{2n}—$ is trimethylene.

12. A compound according to claim 11, wherein $R_3$ and $R_4$ are each hydrogen.

13. A compound according to claim 11, wherein $R_3$ is hydrogen and $R_4$ is fluoro.

14. A compound according to claim 11, wherein $R_3$ is hydrogen and $R_4$ is methyl.

15. A compound according to claim 11, wherein $R_3$ and $R_4$ are each methyl.

16. A compound according to claim 10, wherein $R_1$ is

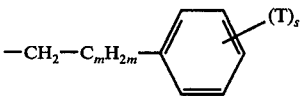

in which $—C_mH_{2m}—$ is methylene.

17. A compound according to claim 16, wherein $s$ is 0.

* * * * *